United States Patent [19]

Koutrouvelis

[11] Patent Number: 5,626,829
[45] Date of Patent: May 6, 1997

[54] METHOD AND APPARATUS FOR INTERSTITIAL RADIATION OF THE PROSTATE GLAND

[75] Inventor: Panos G. Koutrouvelis, McLean, Va.

[73] Assignee: PGK, Enterprises, Inc., McLean, Va.

[21] Appl. No.: 340,288

[22] Filed: Nov. 16, 1994

[51] Int. Cl.[6] .............................. A61K 51/00; A61B 19/00
[52] U.S. Cl. ...................... 424/1.11; 424/1.33; 514/966; 606/130; 606/108
[58] Field of Search ............................ 424/1.11, 1.33; 514/966; 606/130, 108

[56] References Cited

PUBLICATIONS

Medline 94108754 (1993).
Medline 92302534 (1992).

Primary Examiner—Paul J. Killos
Attorney, Agent, or Firm—Fish & Richardson P.C.

[57] ABSTRACT

A method for treating prostate cancer including the steps of placing a patient in the prone position within an imaging device, obtaining regularly spaced two-dimensional images of the prostate gland, placing a needle guiding device adjacent the gluteal region of the patient at an angle substantially identical to an angle of the imaging device, successively placing radioactive seeds within the patient through the gluteal region so as to form a three-dimensional array of seeds encompassing the entire prostate gland, and verifying seed placement using the imaging device.

4 Claims, 3 Drawing Sheets

ND APPARATUS FOR
METHOD AND APPARATUS FOR INTERSTITIAL RADIATION OF THE PROSTATE GLAND

TECHNICAL FIELD OF THE INVENTION

The present invention relates to apparatus and methods for the treatment of prostate cancer and, in particular, to an apparatus and method for prostate brachytherapy.

BACKGROUND OF THE INVENTION

Prostatic cancer has been estimated to affect as many as one in three men. In the U.S. alone, this implies an estimated fifty-million patients who are candidates for treatment of prostatic cancer. Prior methods of treatment include surgical intervention, external radiotherapy, and brachytherapy (interstitial radiation). A general discussion of the localized use of radiation therapy is found in Bagshaw, M. A., Kaplan, I. D. and Cox, R. C., Radiation Therapy for Localized Disease, CANCER 71: 939–952, 1993. Disadvantages associated with surgical intervention include impotence and incontinence. External radiotherapy may have deleterious effects on surrounding normal tissues (e.g., the bladder, the rectum, and the urethra). In contrast, brachytherapy diminishes complications such as impotence and incontinence, and allows a higher and more concentrated radiation dose to be delivered to the prostate gland as compared to external radiotherapy. An additional advantage of brachytherapy is that treatment can be accomplished within a matter of days as compared to weeks, greatly reducing radiation exposure of the adjacent organs.

Prostate brachytherapy can be divided based upon the radiation level used into temporary implantation, which uses high activity sources, and permanent implantation, which uses lower activity sources. These techniques are described in Porter, A. T. and Forman, J. D., Prostate Brachytherapy, CANCER 71: 953–958, 1993. The predominant radioactive sources used in prostate brachytherapy include iodine-125, palladium-103, gold-198, ytterbium-169, and iridium-192. Prostate brachytherapy can also be categorized based upon the method by which the radioactive material is introduced into the prostate. For example, a open or closed procedure can be performed via a suprapubic or a perineal retropubic approach.

SUMMARY OF THE INVENTION

A method for treating prostate cancer, comprising the steps of placing a patient in the prone position within an imaging device, obtaining regularly spaced two-dimensional images of the prostate gland, placing a needle guiding device adjacent the gluteal region of the patient at an angle substantially identical to an angle of the imaging device, successively placing radioactive seeds within the patient through the gluteal region so as to form a three-dimensional array of seeds encompassing the entire prostate gland, and verifying seed placement using the imaging device.

DESCRIPTION OF THE PREFERRED EMBODIMENTS

Preferred embodiments of the invention will now be described with reference to the accompanying figures.

Although transperineal interstitial implantation of the prostate has been widely used, the transgluteal technique for brachytherapy of the prostate provides significant advantages. For example, the transgluteal technique does not require hospitalization or use of an operating room (i.e., may be performed on an out-patient basis). Moreover, transgluteal brachytherapy may be performed under local rather than general or spinal anesthesia. This feature significantly reduces recovery time following the procedure. From an anatomical perspective, transgluteal brachytherapy reduces the risk of prostatic urethra puncture, eliminates interference from skeletal structures during needle insertion, and reduces the need for cystoscopy. All of these factors combine to reduce procedural risk as compared to traditional methods of treating prostate cancer.

In addition to the general advantages of transgluteal brachytherapy, the method of the present invention enhances the accuracy of radioactive seed placement by combining computer aided tomography and a 3-D stereotactic system for precise transgluteal insertion of the seeds in the prostate gland. In addition, verification of needle position prior to and after seed implantation further improves seed placement.

Figure 1:
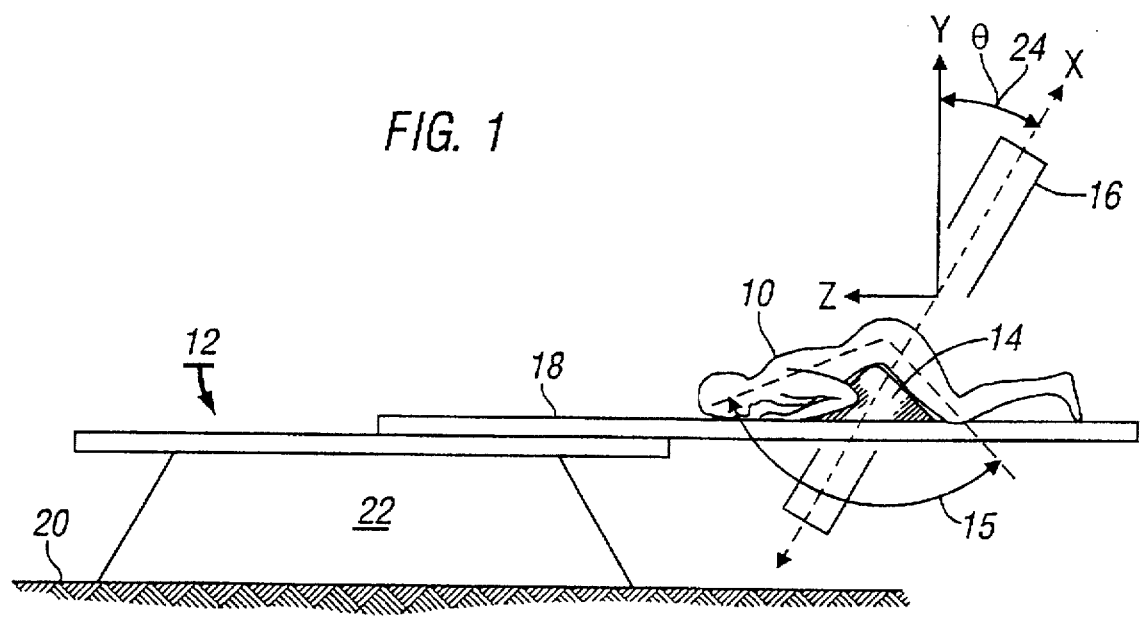
FIG. 1 is a side view of a patient positioned for transgluteal prostate brachytheraphy according to an embodiment of the invention.
Figure 2:
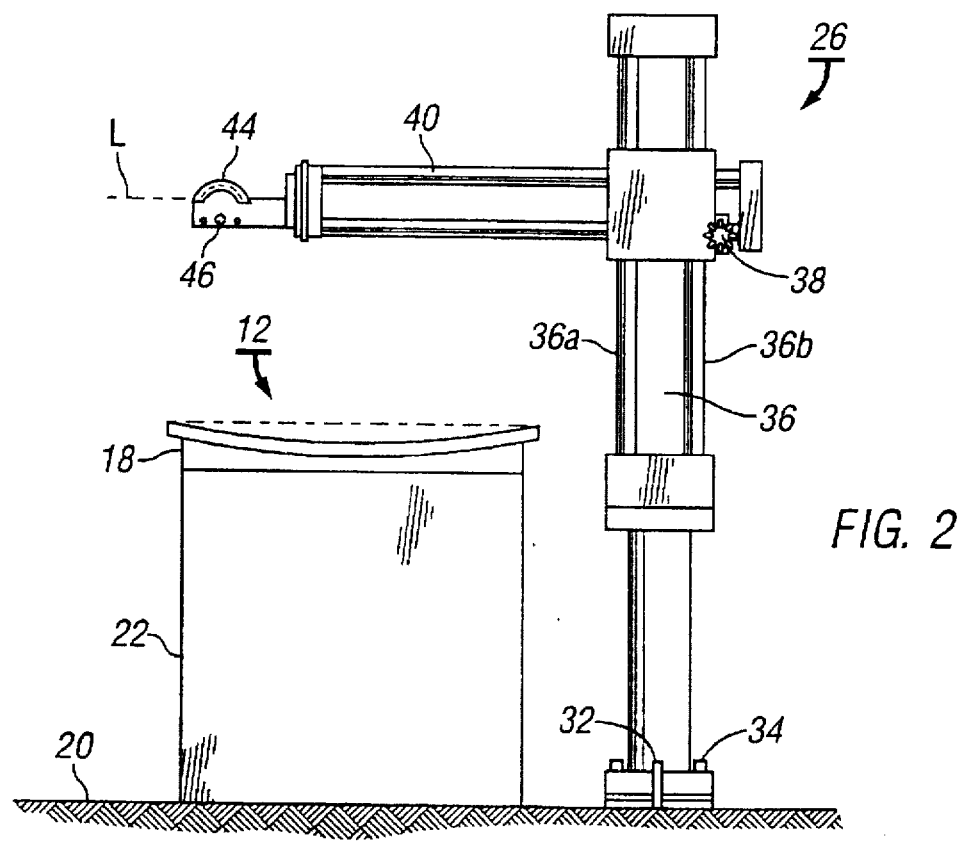
FIG. 2 is an end view of a floor mounted stereotactic device assembly according to an embodiment of the invention.
Figure 3:
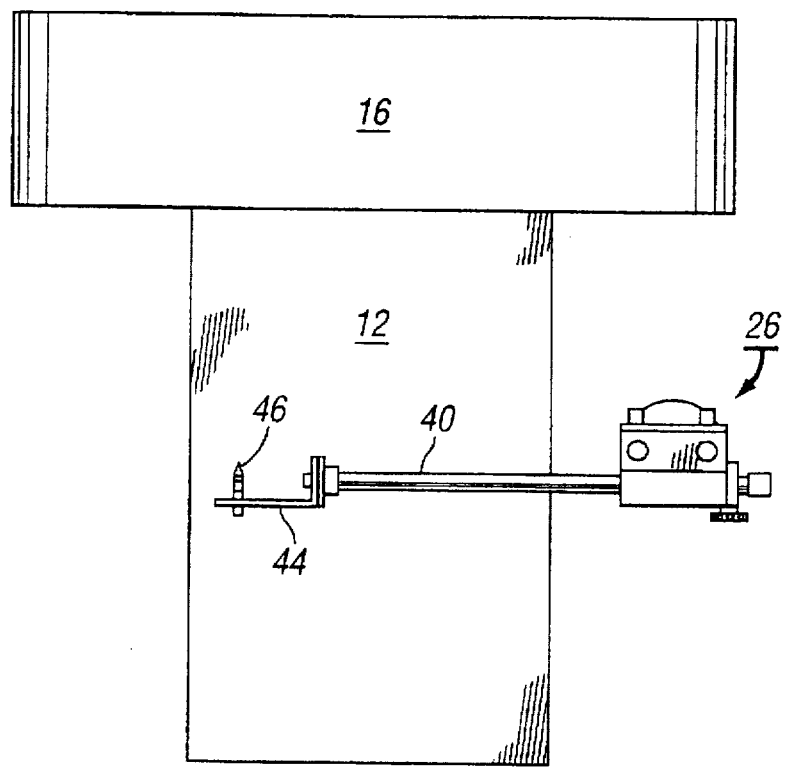
FIG. 3 is a top view of a floor mounted stereotactic device assembly according to an embodiment of FIG. 2.

The brachytherapy method of the present invention (See FIG. 1) includes identifying a patient in need of treatment for prostate carcinoma. A metastatic work-up is then performed including computer-aided tomography (CAT) or magnetic resonance imaging (MRI) of the pelvis and a bone scan. Transgluteal tomographic cuts (5 mm thickness) are obtained by placing the patient 10 in a prone position on the CAT-scan table 12. A pad 14 is placed under the patient's pelvis to raise the gluteal area in an angulation 15. The patient is then placed in the gantry 16 by horizontal displacement (i.e., along the z axis) of the sliding top surface 18 of the table 12. The CAT-scan table 12 is fixed to the floor 20 via the table base 22.

The gantry 16 is tilted at an angle 24 which corresponds to the angulation of the patient's gluteal area (preferably between 26° and 30°). Five millimeter thick tomographic cuts are obtained throughout the prostate beginning at the seminal vesicles. The number of needles, seeds, depth and angulation are determined in a manner described in more detail below.

Prior to treatment, the patient 10 is prepped and draped in the usual manner. Intravenous sedation and local, presacral anesthesia are given by the anesthesiologist. The patient 10 undergoes routine standard monitoring by the anesthesiologist.

Transgluteal tomographic cuts (5.0 mm thickness) are obtained throughout the prostate and seminal vesicles (see above). The patient is then moved out of the gantry and underneath a stereotactic assembly 26 (see FIGS. 2–5). The stereotactic assembly 26 is adjusted to match the tilt of the gantry 24 and is positioned adjacent the gluteal region of the patient 10. A template or needle guide 28, 30 (see FIGS. 6 and 7) is mounted on the stereotactic assembly 26 and a plurality of needles are inserted into the prostate for fixation against the symphysis pubis to reduce prostate motion during subsequent needle insertion. Following fixation of the prostate the template: 28, 30 is disengaged from the stereo tactic assembly 26.

The patient is then moved into the original position under the gantry 6 and repeat tomographic cuts (5.0 mm thickness) are again obtained throughout the prostate. The number of needles to be used, needle depth and angulation, and the number of seeds are calculated using the grid on the CAT-scan monitor, such that the seeds are placed within and surrounding the prostate gland in a three dimensional array averaging one centimeter from center to center. The pre-calculated number of needles are inserted through the template 28 into the prostate using an aseptic technique. The patient is once again moved to the original position in the CAT-scan gantry 16 and repeat tomographic cuts are obtained. The depth of the needles may be adjusted, if necessary, at this time.

The patient is again moved under the stereotactic assembly 26 and the template is reconnected. The pre-calculated number of seeds are then implanted into the prostate using a device such as the MICK applicator (available from, New York Nuclear). The needles are then incrementally extracted so as to achieve seed placement at the desired depths within the prostate. At the completion of the procedure, the needles are removed from the prostate and the patient 10 is removed from under the stereotactic assembly 26.

The floor mounted stereotactic assembly 26 (see FIGS. 2 and 3) of the present invention includes a stanchion 28 coupled to the floor 30 by a plurality of anchor studs 32. Leveling of the stanchion 28 relative to the CAT-scan table 12 is accomplished by a plurality of leveling bolts 34. An upper portion 36 of stanchion 28 comprises two vertical members 36a, 36b. A horizontal support 40 is supported by upper portion 36 in cantilevered fashion and is vertically adjustable along upper portion 36 and is lockable at any desired position therealong. Horizontal support 40 is also movable horizontally with respect to the upper portion 36 through operation of horizontal control knob 38.

A protractor 44 is supported on the distal end of horizontal support 40 and is rotatable relative to the horizontal support 40 about the longitudinal axis L thereof. In addition, a needle guide 46 is mounted on protractor 44 and is angularly adjustable relative thereto. A detailed description of the structure and operation of protractor 44 is found in applicant's U.S. Pat. Nos. 5,047,036 and 5,308,352, which disclose a stereotactic device including a protractor for use in discectomies. The disclosures of U.S. Pat. Nos. 5,047,036 and 5,308,352 are hereby incorporated by reference.

The combination of the vertical and horizontal adjustability of horizontal support 40, the rotatable adjustability of protractor 44, and the angular adjustability of needle guide 46 allow a needle placed within guide 46 to be inserted in a patient at any desired angle. Thus, precise placement of a seed within a patient is made possible through synchronization of angular and positional markings on the stereotactic device with positional information obtained from the grid on the CAT scan monitor.

Figure 4:
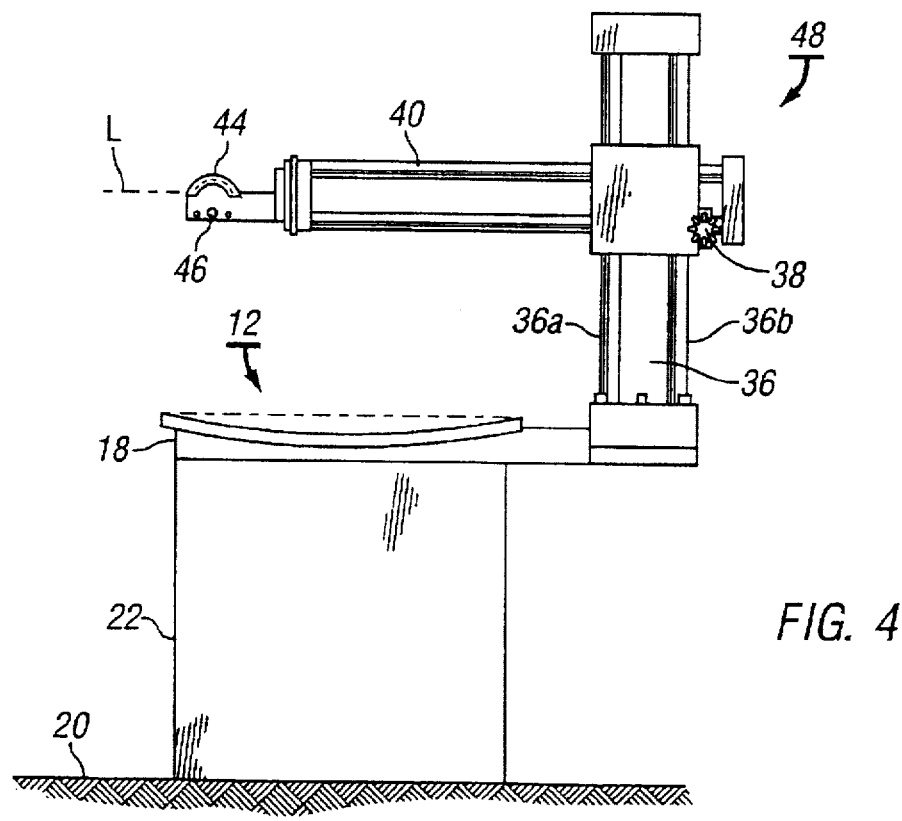
FIG. 4 is an end view of a table mounted stereotactic device assembly according to an embodiment of the invention.
Figure 5:
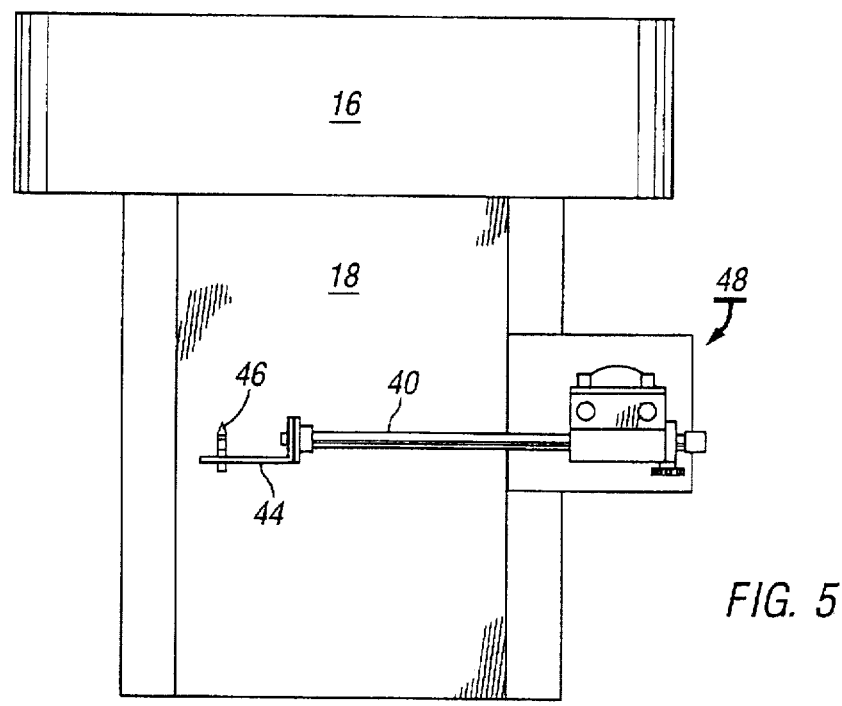
FIG. 5 is a top view of a table mounted stereotactic device assembly according to an embodiment of FIG. 4.

In a preferred embodiment of the invention, the stereotactic assembly 26 is mounted on sliding top surface 18 of Table 12 (see FIGS. 4 and 5). This embodiment allows execution of the brachytherapy procedure to be expedited because the stereotactic device follows the patient into the gantry and thus repeated engagement and disengagement of the stereotactic device is unnecessary.

Figure 6:
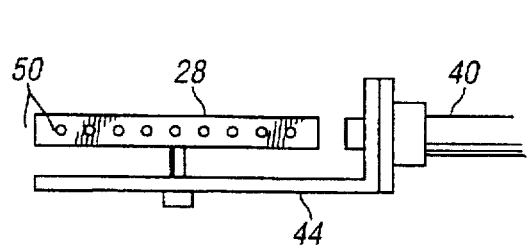
FIG. 6 is a top view of a template mounted on a stereotactic device according to an embodiment of the invention.
Figure 7:
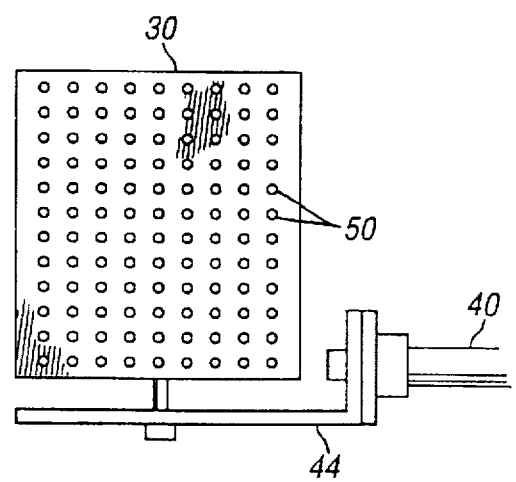
FIG. 7 is a top view of a template mounted on a stereotactic device according to another embodiment of the invention.

Although a needle guide 46 having a single aperture is compatible with the method and apparatus of the present invention, in a preferred embodiment the template comprises a linear array 28, as shown in FIG. 6. Template 28 has apertures 50 at 0.5 centimeter intervals Moreover, the template is approximately 2 centimeters thick to correspond with the thickness of the needle guide 46.

In another embodiment, the template may be a two dimensional linear array 30 having apertures 50 at 0.5 centimeter intervals along two axes. This allows the procedure to be performed more quickly by reducing the set-up time for each needle.

Preferred embodiments of the invention have been disclosed and described in detail. However, the invention is not so limited, but rather is limited only by the scope of the appended claims.

What is claimed is:

1. A method for treating prostate cancer using a stereotactic assembly including a support structure for supporting a protractor in a desired fixed position, the protractor supporting a needle guide, and at least a portion of the stereotactic assembly including the protractor and the needle guide being movable into and out of an imaging device, said method comprising the steps of:

placing a patient in the prone position on a movable surface movable into and out of the imaging device;

moving the movable surface into the imaging device and obtaining at least one two-dimensional image of the prostate of the patient at a predetermined image angle;

removing the movable surface from the imaging device and adjusting the stereotactic assembly such that the needle guide is disposed adjacent the gluteal region of the patient at an angle substantially identical al to said image angle;

placing at least one needle in the vicinity of the prostate of the patient through the gluteal region using the needle guide, thereby engaging the patient and the stereotactic assembly via said needle;

verifying placement of said needle using the imaging device without disengaging said needle from the patient and the stereotactic assembly by moving the movable surface and at least said portion of the stereotactic assembly into the imaging device; and placing radioactive seeds in the vicinity of the prostate using said needle.

2. A method as claimed in claim 1, wherein the step of removing the movable surface from the imaging device and adjusting the stereotactic assembly comprises placing a template adjacent the gluteal region of the patient.

3. A method as claimed in claim 1, further comprising the step of verifying seed placement in the prostate using the imaging device.

4. A method as claimed in claim 2, further comprising the step of placing a plurality of needles through the template into the prostate to reduce prostate motion.

* * * * *

UNITED STATES PATENT AND TRADEMARK OFFICE
CERTIFICATE OF CORRECTION

PATENT NO.   : 5,626,829

DATED        : May 6, 1997

INVENTOR(S)  : Panos G. Koutrouvelis

It is certified that error appears in the above-identified patent and that said Letters Patent is hereby corrected as shown below:

Cover page, item [56] under "PUBLICATIONS"; replace "94108754" with --94108758--.

Column 3, line 10, remove ":";

line 11, remove space between "stereo" and "tactic";

line 13, replace "6" with --16--.

Column 4, line 12, insert --.-- between "intervals" and "Moreover";

line 40, remove "al".

Signed and Sealed this

Sixteenth Day of September, 1997

Attest:

Attesting Officer

BRUCE LEHMAN

Commissioner of Patents and Trademarks